United States Patent [19]

Sampson

[11] Patent Number: 4,851,223
[45] Date of Patent: Jul. 25, 1989

[54] AGRICULTURAL PESTICIDES

[76] Inventor: Michael J. Sampson, 18 Christchurch Road, Norwich, Norfolk, England

[21] Appl. No.: 127,231

[22] Filed: Dec. 1, 1987

Related U.S. Application Data

[63] Continuation of Ser. No. 718,864, Apr. 2, 1985, abandoned.

[30] Foreign Application Priority Data

Apr. 3, 1984 [GB] United Kingdom ............... 8408518
Sep. 11, 1984 [GB] United Kingdom ............... 8422959

[51] Int. Cl.$^4$ .................... A01N 37/00; A01N 59/02
[52] U.S. Cl. .................................... 424/711; 424/713; 514/557
[58] Field of Search ............... 424/162, 164; 514/557

[56] References Cited

U.S. PATENT DOCUMENTS

| 1,614,063 | 1/1927 | Frazier | 424/162 |
|---|---|---|---|
| 3,592,910 | 7/1971 | Clark et al. | 514/481 |
| 3,928,577 | 12/1975 | Kochurova et al. | 424/162 |
| 4,447,984 | 5/1984 | Sampson et al. | 71/92 |
| 4,500,517 | 2/1985 | Luss | 424/162 |

FOREIGN PATENT DOCUMENTS

| 618351 | 3/1927 | France . | |
| 2422331 | 9/1979 | France . | |
| 5437540 | 10/1980 | Japan | 424/162 |

OTHER PUBLICATIONS

Gaur et al.; C.A. vol. 99 (1983) 99:193390c.
Singh et al., C.A., vol. 99 (1983) 99:189,613k.
Sabel'nikova et al., C.A., vol. 73 (1970) 34100e.
Merck Index, 10th ed. (1983) #8411; #8511.

*Primary Examiner*—Allen J. Robinson
*Attorney, Agent, or Firm*—Renner, Otto, Boisselle & Sklar

[57] ABSTRACT

A preservative or sterilant of the type used in the food and/or brewing industry is used to kill pests on crop and ornamental plants comprising applying to them a preservative or sterilant of the type used. Novel compositions contain such a preservative or sterilant together with a coating agent, e.g. di-1-p-menthene, and possibly also a surface-active agent.

6 Claims, No Drawings

AGRICULTURAL PESTICIDES

This is a continuation of application Ser. No. 718,864, filed Apr. 2, 1985, now abandoned.

BACKGROUND TO THE INVENTION

This invention relates to pesticides for use in agriculture and horticulture, including the treatment of ornamental and crop plants.

A number of substances have been used in food and drink preservation and for sterilization of utensils in the food and brewing industries. These include, but are not limited to, the following:

- substances capable of releasing chlorine when dissolved in water, e.g. calcium hypochlorite or sodium hypochlorite;
- substances capable of releasing sulphur dioxide, e.g. sodium metabisulphite (release may be increased by the addition of citric acid to the sodium metabisulphite);
- benzoic acid and salts, e.g. sodium benzoate;
- acetic acid;
- sorbic acid and salts, e.g. sodium sorbate;
- formalin/formaldehyde;
- organic compounds containing chlorine that is released on contact with water, e.g. sodium and other dichloroisocyanurates and Chempro sterilant for home brewing;
- methyl, ethyl and propyl 4-hydroxybenzoates and their sodium salts;
- propionic acid and its salts, e.g. sodium propionate;
- hexamine;
- biphenyl;
- ascorbic acid and its salts, e.g. sodium ascorbate;
- 2-hydroxybiphenyl and its sodium salts (sodium biphenyl-2-yl oxide);
- 2-(thiazol-4-yl)-benzimidazole;
- the nitrate and nitrite of sodium and potassium;
- and nisin.

A list of agents permitted for use in the United Kingdom appears in Statutory Instrument 752 of 1979, (The Food and Drugs Composition and Labelling Preservatives in Food Regulations 1979).

None of these has hitherto been used in controlling fungal or bacterial infection in growing plants, whether grown for crop production or for ornamental purposes.

The effect of these materials lasts only for a short time, sometimes as little as ten minutes, under agricultural conditions. However, such materials are readily available and inexpensive. Many of them are permitted food additives. Moreover, they are non-specific fungicides and bactericides, so that the establishment of resistance to them is unlikely.

Used by themselves at rates from 5 grams to 2.5 kg per hectare they can offer a degree of fungal or bacterial control which is commercially useful in relating to their cost.

BRIEF SUMMARY OF THE INVENTION

The present invention is based on the discovery that materials of the foregoing type can be made into useful pesticides (particularly fungicides and bactericides) of enhanced efficacy, persistance and rainfastness by incorporation together with a coating agent into an agricultural composition. This advantage applies particularly when the sterilant is gaseous, e.g. sulphur dioxide, which is released from sodium metabishulphite, or chlorine, which is released from hypochlorites and dichloroisocyanurates. Such compositions may have a life of 2 hours or so and can usefully sterilize the leaf and surfaces of plants.

DETAILED DESCRIPTION

The preferred coating agent that can be used in accordance with the invention is di-1-p-menthene (which normally occurs in association with its polymers). Other monoterpenes ($C_{10}H_{16}$) can also be used. The agents can be used in admixture with one another.

Apart from monoterpenes, the following compounds are suitable, though this is not an exhaustive list:

1. Terpene hydrocarbons of the elementary composition $C_{15}H_{24}$ (sesquiterpenes)
2. Terpene hydrocarbons of the elementary composition $C_{20}H_{32}$ (diterpenes)
3. Terpene hydrocarbons of the elementary composition $C_{30}H_{48}$ (triterpenes)
4. Terpenes having 40 carbon atoms (tetraterpenes)
5. Bicyclic and tricyclic monoterpenes and their derivatives (e.g. oxygenated derivatives) such as and pinene, d-camphor, d-borneol,d-tanacetone,B-thujone,d- 3-carene
6. Terpene resins (compounded with or without natural or synthetic rubbers)
7. Gum turpentine
8. Sulphate of turpentine
9. Wood turpentine
10. Pineoils
11. Terpineols
12. Non-oxidizing Alkyd Resins, e.g. those of the castor oil, coconut oil, hydrogenated castor oil, lauric acid, oil-free, saturated acid and synthetic fatty acid types
13. Oxidizing Alkyd Resins, e.g. acrylic-resin-modified dehydrated castor oil types, epoxide-resin-modified, isophthalic-acid-based types, linoleic-rich oil type, linseed oil types, linseed oil/dehydrated castor oil types, linseed oil/soya bean oil types, linseed oil/tung oil types, maleic-resin-modified, marine oil types, phenolic-resin-modified, rosin-modified, safflower seed oil types, silicone-resin-modified, soya bean oil types, soya bean oil/tung oil types, styrenated types, sunflowerseed oil types, tall oil types, tobaccoseed oil types, unmodified types, vinyltoluene-modified types and water-soluble types
14. Benzoguanamine resins
15. Styrene polymers and compolymers, e.g. polystyrene and styrene/maleic anhydride and butadiene/styrene copolymer resins
16. Carbamide resins
17. Copal ester resins
18. Coumarone-indene resins
19. Cresylic resins
20. Epoxy resins - e.g. dehydrated castor oil types, linseed oil types, linseed oil/rosin types, phenolic-resin-modified, soya bean oil types, styrenated types, vinyltoluene-modified, and unmodified types as well as those sold under the trade marsk Epikote 205, Epikote 825, Epikote 828 and Epikote 1001
21. Epoxide melamine condensates
22. Epoxide phenolic condensates
23. Ester gums
24. Fumaric resins
25. Furan resins
26. Ketone resins
27. Maleic resins 28. Melamine resins - e.g. butylated types, hexamethoxymethyl types and formaldehyde condensates
29. Metallic rosinates - e.g. calcium or zinc resinates, zinc/calcium mixtures both rosin or modified rosin
30. Phenolic resins and modified phenolic resins - e.g. phenol/aldehyde resole condensates adducted to rosin or modified rosin, as well as phenol/formaldehyde resins
31. Phenoxy resins
32. Polybutadiene resins
33. Polybutene resins
34. Polycarbonate resins
35. Polyisobutylene resins
36. Polyester resins - e.g. polyacrylate and polymethacrylate ester resins
37. Polysulphide resins
38. Polyurethane resins - e.g. modified types and oil-modified types
39. Polyvinyl acetal resins
40. Polyether resins - e.g. polyvinyl ether resins
41. Polyvinly formal resins
42. Rosin derivatives - e.g. esters of rosin, copal, rosin acides or rosin modified by hydrogenation, polymerization isomerization or disproportionation with glycerol, pentaerythritol or other polyhydric alcohols
43. Maleic/fumaric condensate resins - e.g. maleic or fumaric acid/anhydride adducts on rosin or modified rosins, their esters with glycerol, pentaerythritol or other polyhydric alcohols
44. Silicone resins and polymers
45. Urea resins - e.g. urea-formaldehyde
46. Xylene-formaldehyde resins
47. Natural gums/resins - e.g. accoroides, arabic, benzoin, copals, damar, elemi, gamboge, karaya, mastic, rosin, sandarac, shellac and tragacanth
48. Acrylic polymers and copolymers - e.g. polyacrylic acid, polyacrylamide, polyacrylonitrile, poly(methyl methacrylate) and poly(ethyl acrylate/butyl acrylate)
49. Cellulose ethers - e.g. hydroxyethyl cellulose and sodium carboxymethyl cellulose
50. Cellulose esters - e.g. methyl cellulose
51. Hydrocarbon resins - e.g. petroleum resins
52. Polyamide resins
53. Rubbers - e.g. natural rubber, butyl, rubber, nitrile rubber, polychloroprene, rubber/oil emuline and polyurethane rubber and cyclized rubber resins
54. Vinyl polymers and copolymers other than those already mentioned e.g. poly(vinyl acetate), poly(vinyl alcohol), poly(vinyl butyral), poly(vinyl pyrrolidone), poly(vinyl acetate/vinyl chloride) and poly(vinyl acetate/acrylate) and
55. Natural drying oils, with or without metal accelerators - e.g. linseed oil and tung oil and mixtures of them.

Such fungicidal and bacteriocidal substances may be used (with or without a coating agent) in combination with fungicides or bacteriocides commonly used for such purposes in crop plants such as carbendazim, chlorothalonil, propiconazole, triadimefon and benomyl (United Kingdom Ministry of Agriculture, Fisheries and Food Ref Book 380(84)). The fungicidal and bacteriodical substances described in this application may usefully be used in combination with one another.

A surface-active agent, e.g. nonyl phenol ethylene oxide condensate, may also be applied with the fungicide or bactericide, in the presence or absence of a coating agent.

The following Examples illustrate the method and compositions of the present invention.

Twelve aqueous formulations were made up. The first six contained, on a w/v basis, the following ingredients.

Formulation 1: sodium metabisulphite 0.1%
Formulation 2: sodium propionate 0.1%
Formulation 3: sodium ascorbate 0.1%
Formulation 4: sodium metabisulphite 0.1%, sodium propionate 0.05%, sodium ascorbate 0.02%
Formulation 5: sodium benzoate 0.1%
Formulation 6: calcium hypochlorite 0.1%.

Formulations 1A to 6A corresponded respectively to each of Formulations 1 to 6, but each of them also contained, on a v/v basis, 0.25% of di-1-p-menthene and 0.025% of nonyl phenol ethylene oxide condensate.

Formulations 1A to 6A are in accordance with the present invention.

The twelve formulations were used to control powdery mildew (*Erisiphe graminis*) on spring barley, var. 'Triumph'. The plants were sprayed as soon as mildew development was seen. The plants were scored from 0(no control) to 10 (100% control) two weeks later.

| Formulation No. | 1 | 1A | 2 | 2A | 3 | 3A | 4 | 4A | 5 | 5A | 6 | 6A |
|---|---|---|---|---|---|---|---|---|---|---|---|---|
| Mildew Control Score | 3 | 7 | 3 | 6 | 3 | 5 | 5 | 10 | 3 | 6 | 3 | 5 |

It will be seen that the Examples of the invention were superior to the corresponding compositions containing no coating agent, but that those compositions are all effective in providing some mildew control.

I claim:

1. An aqueous fungicidal composition comprising: about 0.1% on a w/v basis of sodium metabisulphite; about 0.05% on a w/v basis of sodium propionate; about 0.25% on a v/v basis of di-1-p-menthene; and about 0.025% on a v/v basis of nonyl phenol ethylene oxide condensate.

2. A method for combatting fungi on ornamental or crop plants comprising spraying said plants with a fungicidally effective amount of an aqueous composition comprising: about 0.1% on a w/v basis of sodium metabisulphite; about 0.05% on a w/v basis of sodium propionate; about 0.25% on a v/v basis of di-1-p-menthene; and about 0.025% on a v/v basis of nonyl phenol ethylene oxide condensate.

3. An aqueous fungicidal composition comprising: about 0.1% on a w/v basis sodium metabisulphite; about 0.25% on a v/v basis of di-1-p-menthene; and about 0.025% on a v/v basis of nonyl phenol ethylene oxide condensate.

4. An method for combatting fungi on ornamental or crop plants comprising spraying said plants with a fungicidally effective amount of an aqueous fungicidal composition comprising: about 0.1% on a w/v basis sodium metabisulphite; about 0.25% on a v/v basis of di-1-p-menthene; and about 0.025% on a v/v basis of nonyl phenol ethylene oxide condensate.

5. An aqueous fungicidal composition comprising: about 0.1% on a w/v basis sodium propionate; about 0.25% on a v/v basis of di-1-p-menthene; and about 0.025% on a v/v basis of nonyl phenol ethylene oxide condensate.

6. An method for combatting fungi on ornamental or crop plants comprising spraying said plants with a fungicidally effective amount of an aqueous fungicidal composition comprising: about 0.1% on a w/v basis sodium propionate; about 0.25% on a v/v basis of di-1-p-menthene; and about 0.025% on a v/v basis of nonyl phenol ethylene oxide condensate.

* * * * *